(12) United States Patent
Tredinnick et al.

(10) Patent No.: US 12,324,592 B2
(45) Date of Patent: Jun. 10, 2025

(54) VETERINARY SURGICAL GUIDE

(71) Applicant: Ossability Limited, Christchurch (NZ)

(72) Inventors: Seamus John Tredinnick, Christchurch (NZ); Brent Michael Higgins, Christchurch (NZ)

(73) Assignee: Ossability Limited, Christchurch (NZ)

( * ) Notice: Subject to any disclaimer, the term of this patent is extended or adjusted under 35 U.S.C. 154(b) by 97 days.

(21) Appl. No.: 18/018,765

(22) PCT Filed: Jul. 30, 2021

(86) PCT No.: PCT/NZ2021/050118
§ 371 (c)(1),
(2) Date: Jan. 30, 2023

(87) PCT Pub. No.: WO2022/025775
PCT Pub. Date: Feb. 3, 2022

(65) Prior Publication Data
US 2023/0301663 A1  Sep. 28, 2023

(30) Foreign Application Priority Data
Jul. 31, 2020 (NZ) .................................. 766751

(51) Int. Cl.
*A61B 17/15* (2006.01)
*A61B 90/00* (2016.01)
*A61D 1/00* (2006.01)

(52) U.S. Cl.
CPC .......... *A61B 17/152* (2013.01); *A61B 17/157* (2013.01); *A61B 90/03* (2016.02);
(Continued)

(58) Field of Classification Search
CPC ......................................... A61B 17/15–17/158
See application file for complete search history.

(56) References Cited

U.S. PATENT DOCUMENTS

| 1,389,556 A | * | 8/1921 | Winn ....................... G01B 3/56 |
| | | | 33/417 |
| 4,952,214 A | * | 8/1990 | Comparetto ........... A61B 17/15 |
| | | | 606/82 |

(Continued)

OTHER PUBLICATIONS

Australian Examination Report 1 for corresponding Australian Application No. 2021315403 dated Dec. 5, 2023.
(Continued)

*Primary Examiner* — Zade Coley
(74) *Attorney, Agent, or Firm* — Harness, Dickey & Pierce, P.L.C.

(57) ABSTRACT

The invention relates to a surgical guide for receiving and guiding a surgical instrument performing a bone osteotomy, the guide including a body, at least one cutting channel extending in length along the first body face and extending through the body, the cutting channel having a discrete length such that the channel is bounded by the first and second body faces through which it extends, two or more apertures adapted to receive a fixation device, the guide including one or more elongate arms or arm assemblies directly or indirectly connected to and extending from one side wall of the body. The guide may be used in canine tibial plateau levelling osteotomy and other orthopedic or surgical procedures. Also described are methods for use of the guide.

16 Claims, 10 Drawing Sheets

(52) U.S. Cl.
CPC ............... *A61B 90/08* (2016.02); *A61D 1/00* (2013.01); *A61B 2090/036* (2016.02); *A61B 2090/0807* (2016.02)

(56) References Cited

U.S. PATENT DOCUMENTS

| | | | |
|---|---|---|---|
| 5,578,038 A | 11/1996 | Slocum | |
| 5,643,270 A * | 7/1997 | Combs | A61B 17/1637 606/86 R |
| 6,007,537 A * | 12/1999 | Burkinshaw | A61B 17/155 606/88 |
| 8,529,571 B2 * | 9/2013 | Horan | A61B 17/157 606/87 |
| 8,690,881 B2 * | 4/2014 | Axelson, Jr. | A61B 17/1764 623/20.14 |
| 2010/0160919 A1 * | 6/2010 | Axelson, Jr. | A61B 17/155 606/89 |
| 2010/0318088 A1 | 12/2010 | Warne et al. | |
| 2013/0331845 A1 * | 12/2013 | Horan | A61B 17/15 606/88 |
| 2017/0156741 A1 * | 6/2017 | Liu | B33Y 80/00 |
| 2018/0028272 A1 * | 2/2018 | Tredinnick | A61B 17/1764 |
| 2019/0070005 A1 | 3/2019 | Brailovski et al. | |
| 2020/0113581 A1 * | 4/2020 | Duerr | A61B 90/10 |

OTHER PUBLICATIONS

Australian Examination Report 2 for corresponding Australian Application No. 2021315403 dated Mar. 7, 2024.

Australian Notice of Acceptance for corresponding Australian Application No. 2021315403 dated Mar. 26, 2024.

International Search Report of the ISA and Written Opinion issued in PCT/NZ2021/050118, mailed Nov. 10, 2021; ISA/AU.

* cited by examiner

VETERINARY SURGICAL GUIDE

CROSS-REFERENCE TO RELATED APPLICATIONS

This application is a 371 U.S. National Phase of International Application No. PCT/NZ2021/050118, filed on Jul. 30, 2021, which also claims priority to New Zealand Patent Application 766751 filed on Jul. 31, 2020. The entire disclosure of the above application is incorporated herein by reference.

FIELD OF INVENTION

This invention relates to a surgical guide. More specifically, the invention relates to a surgical osteotomy guide that may be used in canine tibial plateau levelling osteotomy and other orthopedic or surgical procedures.

BACKGROUND TO THE INVENTION

Following a canine cranial cruciate ligament rupture, joint stability in the knee is compromised. To address the instability, a tibial plateau levelling osteotomy (TPLO) may be performed to change the angle of the tibial bone to level off the knee joint, creating a flat joint that allows for less shearing movement following a cranial cruciate rupture.

In the TPLO procedure, an arcuate cut is made in the proximal end of the tibia to mobilise the tibial plateau, which is then rotated so that its slope changes to approximately 5 degrees from the transverse plane (normal to the tibial axis). The new rotated position of the tibial plateau prevents the femur from sliding backwards during weight bearing and the joint is stabilised, without the need for the cruciate ligament. The repositioned tibial plateau is held in place using a plate connecting the tibia and the newly aligned tibial plateau section.

The arcuate cut required in the proximal end of the tibia is very commonly created freehand with a radial saw blade, often with the surgeon using their thumb as a guide. This method introduces obvious room for error and also does not translate well between left and right TPLO surgeries, with the cut one side more easily and accurately performed depending on the handedness of the surgeon.

Alignment jigs for TPLO surgeries such as those outlined in U.S. Pat. No. 8,529,571 are known. Alignment guides such as this are cumbersome to use as they have multiple moving parts that require securing in different positions in order to place the arcuate cutting surface where required. The amount of guide extending outwardly from the tibia is significant and decreases working space at the surgical site. In addition, the alignment jig shown in U.S. Pat. No. 8,529,571 does not provide a means to secure the arcuate saw within the guide when cutting, but relies on the practitioner following a one-sided curve the saw can abut against. Without the saw blade being guided on both sides of the blade, errors in the radial bone cut are more likely to occur as the blade can stray from the guide.

Similarly, U.S. Pat. No. 5,578,038 provides an alignment guide for making the curvilinear tibial cut required in TPLO surgeries. The jig described in U.S. Pat. No. 5,578,038 consists of a positioner structure for positioning adjacent a portion of the tibia, and an aligner structure for adjusting the jig position.

Additional elongate members may also be included in the guide, with the different members of the guide moveable with respect to each other to create a range of different angles and guide positions to aid in the TPLO procedure.

Having a number of different moveable parts within the guide that need to be separately moved and positioned to accommodate different scenarios is both time consuming and creates additional room for error as each individual separate part is moved.

It would be advantageous to have a TPLO guide that does not require multiple moving parts and may be used to successfully guide a radial osteotomy across a range of animal shapes and sizes during an orthopedic procedure such as the TPLO.

OBJECT OF THE INVENTION

It is an object of the invention to provide a surgical guide that provides a set of parameters for guiding tibial osteotomies in TPLO and other orthopedic procedures.

Alternatively, it is an object of the invention to at least provide the public with a useful choice.

SUMMARY OF THE INVENTION

According to one aspect of the invention, there is provided a surgical guide for receiving and guiding a surgical instrument performing a bone osteotomy, the guide including;
  a body, the body including a first body face and an opposing second body face adapted to abut the patient bone when in use, the first and second faces separated by one or more side walls;
  at least one cutting channel extending in length along the first body face and extending through the body from the first body face to the second body face, the cutting channel having a discrete length such that the channel is bounded by the first and second body faces through which it extends;
  two or more apertures extending from the first body face through the body to the second body face, the apertures adapted to receive a fixation device;
  wherein the guide includes one or more elongate arms or arm assemblies directly or indirectly connected to and extending from the same side wall of the body.

In preferred embodiments, the body is substantially arcuate in shape.

Preferably, the body includes a single arcuate cutting channel.

Optionally, the guide includes a second cutting channel extending through the body from the first body face to the second body face. More preferably, the second cutting channel is a straight channel.

Alternatively, the body includes one or more straight cutting channels and/or or more arcuate cutting channels.

In alternative embodiments the cutting channels may be angled greater or less than 90 degrees between the first and second faces.

In various embodiments, the elongate arms are integrally formed with the body, or may be removably connected using a mechanical connection means such as a clip-fit or interference fit.

In preferred embodiments, the one or more elongate arms include a first arm face and an opposing second arm face adapted to abut patient bone when in use, the first and second arm faces separated by one or more side walls; and one or more apertures extending from the first arm face through the arm(s) to the second arm face, the apertures adapted to receive a fixation device.

In further preferred embodiments, the guide includes two elongate arms extending from the body, each arm including between 1-20 cylindrical apertures spaced along the length of each arm.

In more preferred embodiments, the surgical guide includes an arcuate body portion having a convex side wall and an opposing concave side wall; and, two arms connected to the convex side wall such that the first body face and the first arm face are substantially level with each other.

More preferably, the two arms are connected at a first end via a bridge portion to form a V or U-shaped arm assembly. Even more preferably, the V or U-shaped arm assembly is connected to the convex side wall at or near the bridge portion of the V or U-shaped arm assembly.

Preferably, the V or U-shape arm assembly is centrally connected to the convex side wall.

More preferably, the U or V-shaped arm assembly is connected to the convex side wall at the base of the V or U-shape body via a neck. Even more preferably, the neck is shaped to create one or more recesses between the arm assembly and the body of the guide.

More preferably, the recess is shaped to receive a locating means such as a pin, needle, wire or drill bit. Even more preferably, the recess is V-shaped or U-shaped.

Preferably, the guide includes three cylindrical apertures, the three apertures positioned on the same side of the arcuate cutting channel. More preferably, the three apertures are located proximate the concave side of an arcuate cutting channel.

More preferably, the guide includes two angled cylindrical apertures converging towards a central cylindrical aperture.

Preferably, the second face of the body is shaped to conform to the anatomical surface of the patient that the second face abuts in use.

Alternatively, the second face includes one or more steps, ridges, contours, or flanges to alter the shape of the second face.

In further preferred embodiments, the body includes at least one side wall including contours in the wall. More preferably, the body includes a side wall including sidewalls shaped to abut a tibial medial condyle.

In other embodiments, the body side walls may include one or more raised or depressed features such as projections, ribs, recesses or bumps to help guide rotation of the surgical guide in use.

Preferably, the second arm face is contoured or curved.

In further preferred embodiments, the body includes rotational measurement markings on one or more side walls.

In further embodiments there is provided a method for guiding an osteotomy tool using the surgical guide described above, the method including the steps of;
determining one or more preferred osteotomy positions on a patient body;
aligning the guide with an anatomical location on a patient;
fixing the guide in position on a patient using one or more apertures on the surgical guide;
guiding the osteotomy tool through or partially through the at least one cutting channel in the surgical guide.

In still further embodiments there is provided a method for making an ostetomy during a canine TPLO procedure using the surgical guide described above, the method including;
determining one or more preferred osteotomy positions on a canine tibia;
aligning the guide with an anatomical location on the canine;
fixing the guide in position on the tibial plateau using one or more apertures on the surgical guide;
guiding the osteotomy tool through or partially through the at least one cutting channel in the surgical guide to fully remove the tibial plateau;
rotating the tibial plateau and guide to a predetermined mark on the surgical guide;
securing the tibial plateau in the new location using a fixation tool; and
removing the surgical guide.

Preferably, the method includes the step of configuring the guide based on the osteotomy position determined at a) before alignment step b).

In preferred embodiments the predetermined mark at step e) is a pin or wire, and the tibial plateau and guide are rotated until the pin abuts the neck of the surgical guide.

For the purposes of this specification, reference to the tibial plateau should be taken to mean a segment of the proximal tibia including the proximal tibial joint surface and bone adjacent the proximal tibial joint surface. The exact size and shape of the tibial plateau will be determined by the bone segment removed by the surgeon and will vary between patients.

Further aspects of the invention, which should be considered in all its novel aspects, will become apparent to those skilled in the art upon reading of the following description which provides at least one example of a practical application of the invention.

BRIEF DESCRIPTION OF THE DRAWINGS

One or more embodiments of the invention will be described below by way of example only, and without intending to be limiting, with reference to the following drawings, in which.

DETAILED DESCRIPTION OF PREFERRED EMBODIMENTS OF THE INVENTION

The surgical guide of the present invention will be described further in non-limiting terms below with reference to FIGS. 1-10.

The surgical guide of the current invention may be used for guiding an osteotomy during a canine tibial plateau levelling osteotomy (TPLO) procedure. The surgical guide and variations thereof may also be used in other surgeries, for example CORA based levelling osteotomy (CBLO), tibial tuberosity advancement (TTA), circular tibial tuberosity advancement (cTTA), modified Maquet procedure (MMP), tibial tuberosity transposition (TTT), or in cranial tibial wedge osteotomy (CTWO) procedures.

For explanatory purposes the description below will refer to the use of the guide when performing a TPLO procedure, however this is not intended to be limiting in any way. The surgical guide may be used as a guide for a range of surgical procedures in both animals and humans where a guide is required for drill or pin placement, performing an osteotomy or for guiding any other suitable instrumentation.

Figure 1:
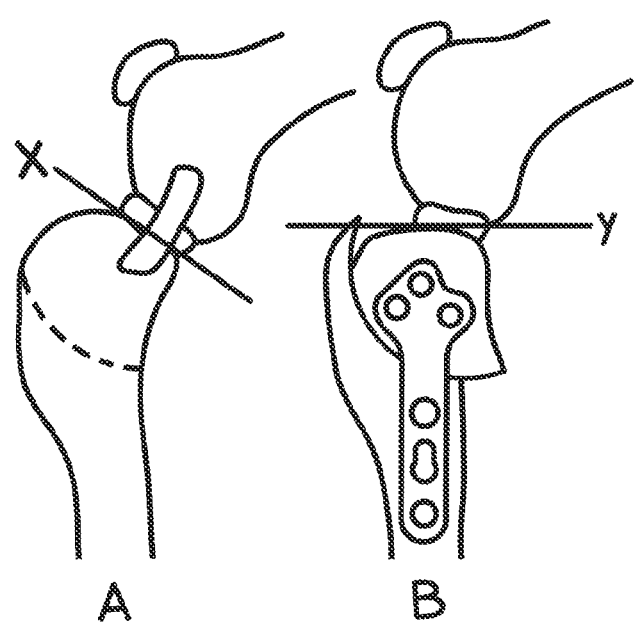
FIG. 1 shows a before and after demonstration of a TPLO procedure using known techniques.

The basic principles of the TPLO procedure are shown in FIG. 1. TPLO surgery is typically undertaken by veterinarians as a result of a cranial cruciate ligament rupture, most commonly in dogs. The cranial cruciate ligament prevents backward movement of the femur relative to the tibia, and when damaged, the backward movement of the femur across the downward sloping tibial plateau results in significant pain for the animal. The TPLO procedure realigns the angle of the tibial plateau, reducing the ability of the femur to slide backwards and stabilising the joint.

In the TPLO procedure, as seen in A of FIG. 1, an arcuate osteotomy is made across the tibial plateau, as shown by the dashed line. The initial angle of the tibial plateau is indicated by X. Once the tibial plateau is removed, the removed bone segment may be rotated across the cut tibia to a new position as shown in B and fixed into position. The angle of the tibial plateau is then significantly reduced (Y), preventing the femur from sliding down the tibial plateau surface when weight is placed on the joint.

Both the positioning and direction of the arcuate cut and the subsequent rotation of the tibial plateau are important in a successful TPLO procedure. The surgical guide of the present invention enables a successful TPLO procedure by providing a way to perform these steps with ease and accuracy.

Figure 2:
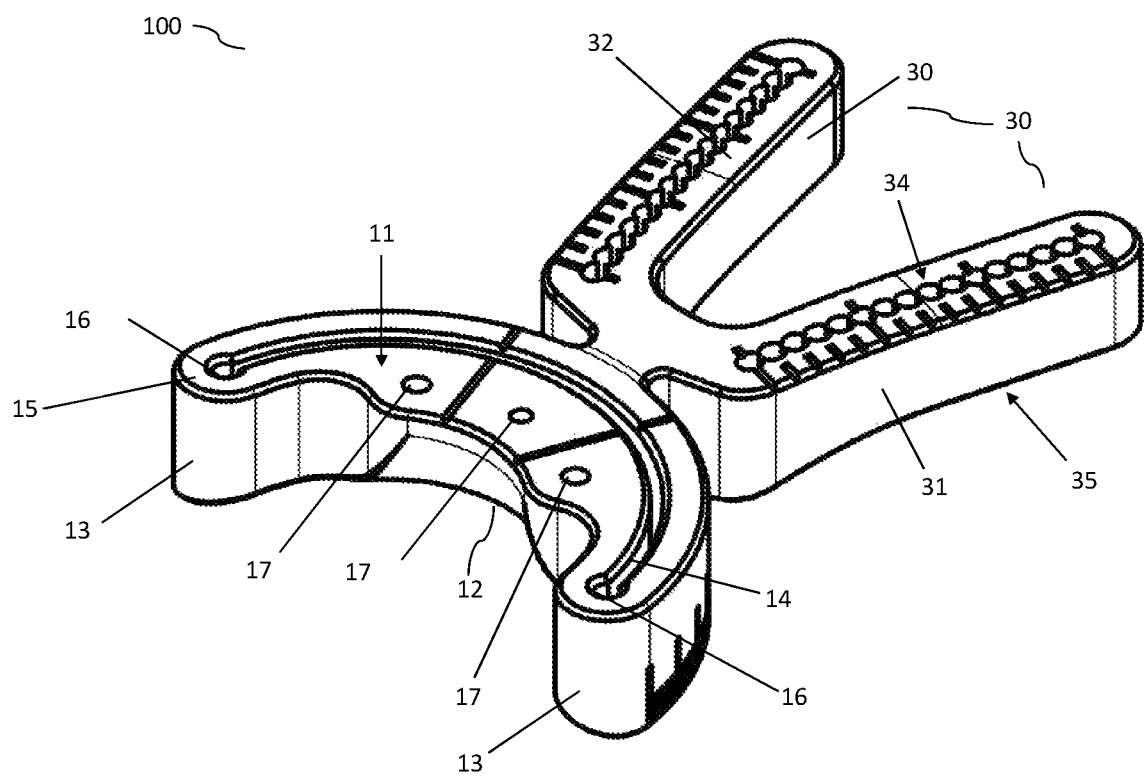
FIG. 2 shows a top perspective view of the surgical guide in one embodiment of the present invention.
Figure 3:
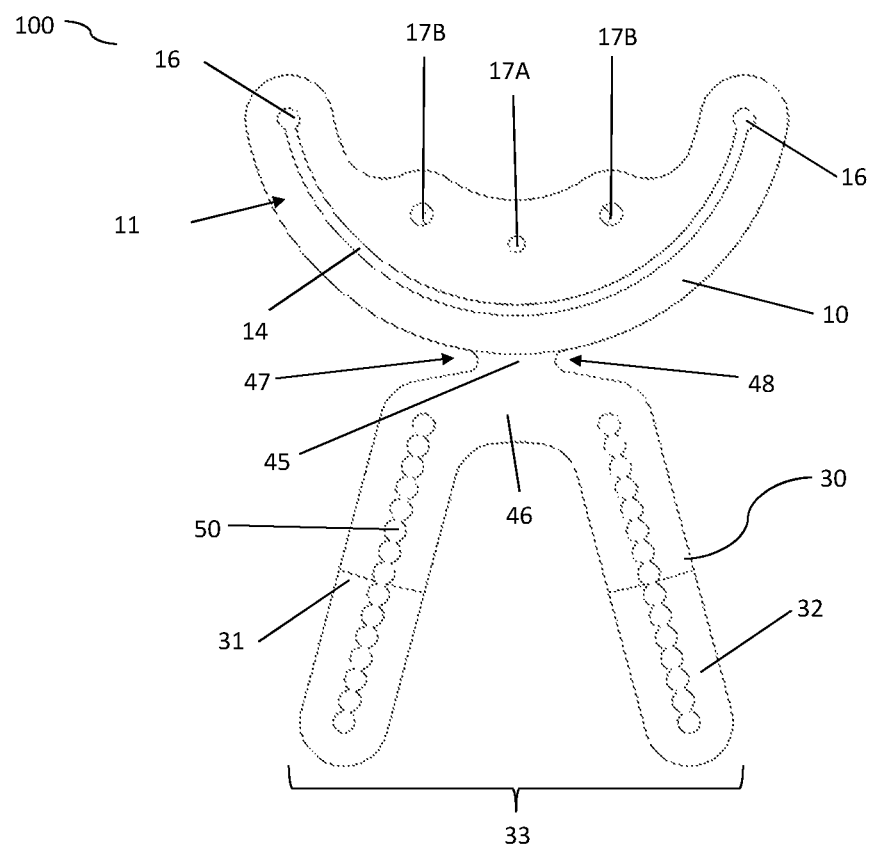
FIG. 3 shows a top view of the guide of FIG. 1.

FIGS. 2 and 3 show the surgical guide 100 in a preferred form of the invention. Guide 100 includes body 10 and arms 30.

Body 10 includes a first body face 11 and opposing second body face 12 separated by side walls 13. In use, body 10 is placed on a patient bone such that second body face 12 abuts the patient bone being cut, with first face 11 facing out from the patient towards the surgeon.

Body 10 is preferably arcuate in shape, with the curve of the arcuate shape ranging between a circular or elliptical arc depending on the size of the guide required and the shape of the osteotomy being conducted. The guide body may also take other shapes provided such a shape can receive a cutting channel, such as irregular rectangular prisms, preferably with curved or softened vertices.

A cutting channel 14 extends through body 10 from first face 11 through to second face 12, forming a channel through body 10. Body 10 is preferably solid, but may be formed with a porous material, be supported with internal ribs or walls, or may be substantially hollow, depending on the materials used for manufacture.

Cutting channel 14 may be straight, angled, curved or have an arcuate shape depending on the surgery the guide will be used for. It is envisaged that a single guide may also have multiple cutting channels so that a number of different osteotomies may be performed using the same guide if required. Cutting channels may also extend perpendicular to the first and second faces through the body, or may be angled greater or less than 90 degrees from the first or second face as they extend between the first face 11 to second face 12, guiding a saw blade to form and angled cut in the bone below. The angle of the cutting channel may change depending on the surgical requirements.

In further variations, the cutting channel may be contoured to suit the saw blade being utilised, or multiple cutting channels are incorporated that merge or angle towards or away from each together such that a section of bone may be removed from between the channels.

For a TPLO procedure, and as shown in FIGS. 2 and 3, cutting channel 14 is arcuate and extends along almost the full arc of body 10, but does not extend through any side walls 13. Each end 16 of cutting channel 14 terminates before meeting a side wall 13, leaving region 15 of the body intact to form a barrier between the cutting channel and the external tissue. This body region 15 ensures a saw blade cannot accidentally slip further than the channel and damage surrounding tissue. This is particularly important in the knee region where major arteries are present close to the surgical site. For stability of the guide, cutting channel 14 should terminate 2 mm-5 mm before the edge of body 10. The width of cutting channel 14 is preferably between 0.5 mm-5 mm, suitable for receiving a saw blade of standard width.

Body 10 further includes one or more apertures 17. Apertures 17 are adapted and shaped to receive a fixation device such as a pin or wire, securing body 10 in the correct position on the patient bone. For the TPLO shaped guide of FIGS. 2-10, three apertures extend through body 10, from first face 11 to second face 12 and are preferably cylindrical in shape.

Apertures 17 are positioned on the concave side of cutting channel 14, such that when guide 100 is positioned on a proximal tibia 102 and an incision is made through cutting channel 14, body 10 is secured to the portion of tibial bone 102 that has been removed. This is shown more clearly in FIGS. 9 and 10.

In alternative embodiments where different surgeries are being performed, different animals, or different sized animals are used, or different shaped cutting channels are employed, the aperture position may change according to best placement of fixation devices.

As seen in FIG. 3, the preferred embodiment includes a central aperture 17A for initial placement of guide 100, with a further apertures 17B located either side of the central aperture 17A. Apertures 17B may be angled towards aperture 17A, such that pins inserted into bone through these apertures converge, securing the guide into a fixed position on the bone.

Figure 4:
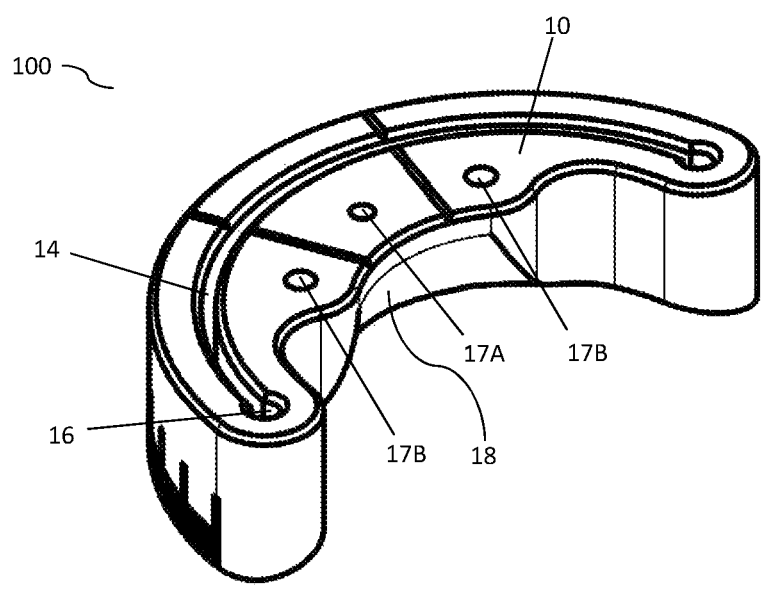
FIG. 4 shows an end perspective view of the surgical guide in an alternative embodiment.
Figure 5:
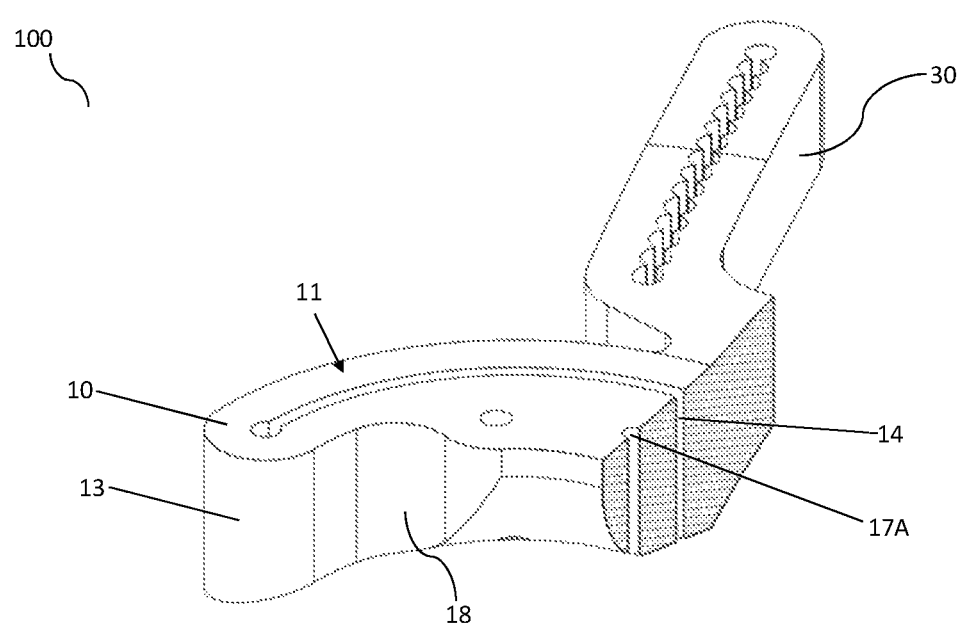
FIG. 5 shows a cross section of the perspective view of the guide of FIGS. 2 and 3.
Figure 7:
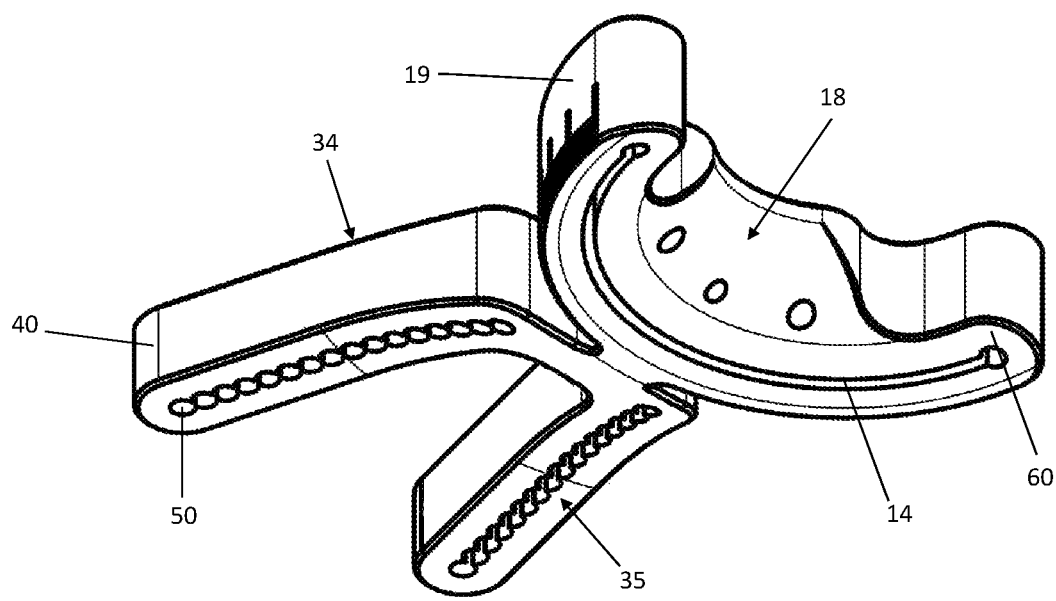
FIG. 7 shows a bottom perspective view of the guide of FIGS. 2, 3, 5 and 6.

The side walls 13 of body 10 may be smooth, textured or contoured. As seen in FIGS. 4, 5 and 7 the body side wall at 18 is contoured to enable body 10 to be placed closely against the tibial condyle, ensuring the best possible positioning of guide 100. Second face 12 of body 10 may also include anatomy specific contours to enable a close connection between guide 100 and the surface of the surgical site. Soft tissue/fibrous capsule interference is also mitigated by contouring the side walls to the anatomy on which it sits. Steps or flanges may be incorporated into either the side walls or second face 12 to act as spacers, addressing issues such as medial patella luxation.

The surgical guide of the invention includes arms 30 (described in more detail below) that may be integrally formed or removable. FIG. 4 shows a variation with guide 100 formed from body 10, without the additional arm supports seen in earlier figures. The core features necessary for performing a guided TPLO procedure are retained, with apertures 17A, 17B, cutting channel 14 and curved side walls 18 shown.

FIG. 5 shows a cross section of guide 100 centrally separating the body 10 and one arm 30. Aperture 17A and cutting channel 14 are shown extending through body 10 from first face 11 to second face 12, allowing a fixation pin and osteotomy saw respectively to extend through the aperture and channel to the bone beneath. In this embodiment, guide 100 is substantially solid.

Figure 6:
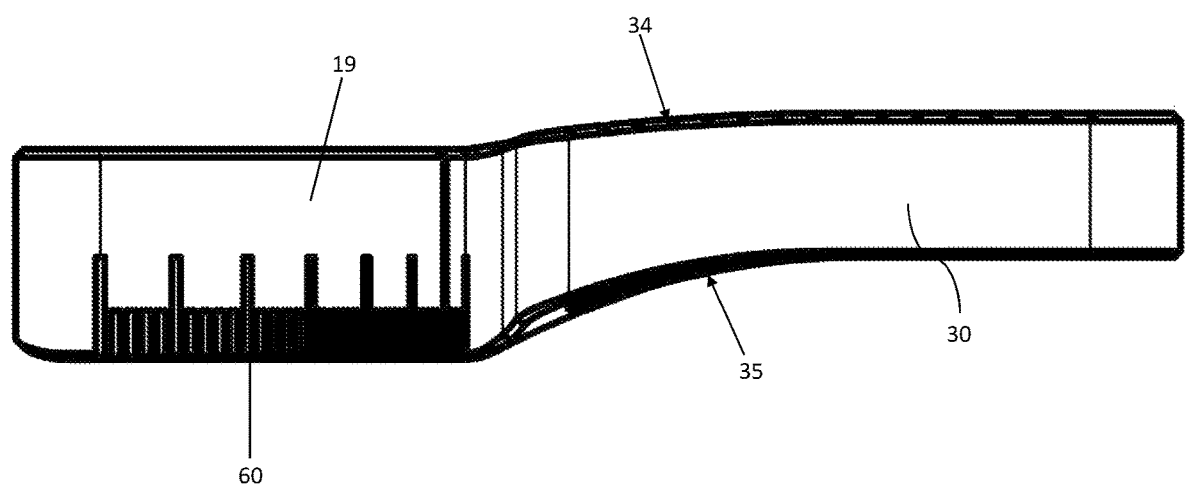
FIG. 6 shows a side view of the guide of FIGS. 2, 3 and 5.
Figure 8:
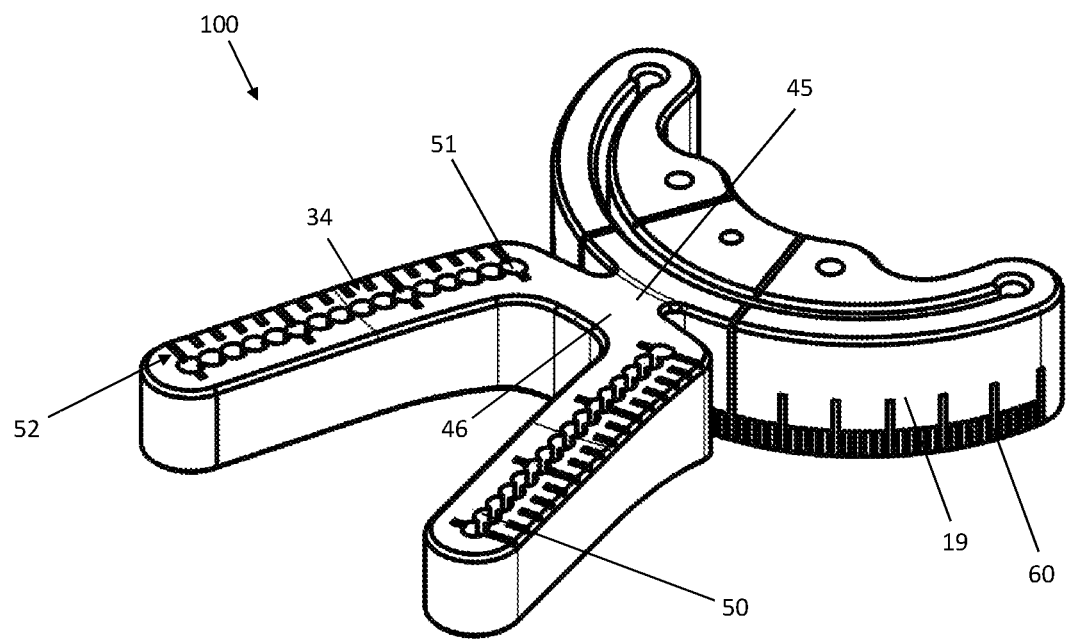
FIG. 8 shows a rear perspective view of the guide of FIGS. 2, 3 and 5-7.

Body 10 may include rotation markings 60, as seen most clearly in FIGS. 4, 6 and 8. On a guide designed to be used for the TPLO procedure, rotation markings 60 are placed on side wall 19, the convex side wall of body 10. Preferably, the markings are in mm increments and extend the full length of side wall 19, extending around the side wall 19 from where arms 30 are connected to body 10 in one or both directions as seen in FIG. 8. For embodiments with removable arms 30, rotation markings may be incorporated across the body side wall under the arm connection region. Rotation markings 60 provide a means to determine the extent of rotation applied to the tibial condyle once removed by osteotomy.

Guide 10 preferably includes one or more elongate arms 30, seen in FIGS. 2-3, 5-10. Arms 30 assist with locating guide 10 in position on the tibia and may be integrally formed with body 10, or may be removable using a mechanical connection means. Having removable arms 30 provides the option of either using body 10 only, or possibly beginning a surgical procedure with arms 30 in place to enable accurate positioning of body 10, then removing arms 30 once body 10 has been secured in position on the bone. This may be useful in situations where there is limited room at the surgical site, or where a smaller device is preferable.

Arms 30 are formed with, or are connected to body 10 such that arms 30 extend from the same side of body 10 and extend in generally the same direction, although they may be angled from each other. Arms 30 may be removably connected to body 10 using known connections techniques, including slip-fit mechanisms, interference fit, pins, screws, clasps or clamps. When non-removable, arms 30 are preferably integrally formed with body 10 as a single piece construction.

An arm assembly 33 is shown in FIGS. 2, 3 and 5-10 as a preferred embodiment. Arm assembly 33 includes two elongate arms 31, 32, each having a first arm face 34 and an opposing second arm face 35 adapted to abut patient bone when the guide is in use. The first 34 and second 35 arm faces separated by one or more arm side walls 40. Side walls 40 are preferably the same or similar width to side walls 18 of body 10, although as seen in FIG. 6, second arm face 35 may be curved or contoured to correspond to the shape of the patient anatomy over which the guide is placed. First arm face 34 is preferably substantially level with first body face 11, such that a continuous first face is created across guide 100 between the body 10 and arms 30.

Arm assembly 33 comprises two elongate arms 31 and 32, each arm connected at a first end to form a V or U-shaped arm assembly. A bridge portion 46 connects arms 31 and 32, the length of bridge portion 46 between arms 31 and 32 being sized to space arms 31 and 32 as far or as close together as required. For example, increasing the length of bridge portion 46 results in the arm assembly having a more U-shaped form, while decreasing the length results in a more V-shaped form to the arm assembly. Bridge portion 46 is formed in the same manner of arms 31 and 32, with a first face and second opposing face separated by side walls, such that arm assembly 33 is continuously formed as a single piece, either in conjunction with, or separately from body 10.

Arms 31 and 32 may be parallel to each other or angled apart on their elongate axis. In the preferred embodiments, arms 31 and 32 are positioned to form an acute angle between the end of each arm distal from bridge portion 46, and the centre of bridge portion 46. More preferably, the acute angle is 10-60°.

Bridge portion 46 of arm assembly 33 connects to arcuate body 10 at or near the centre of the convex side wall 19 at neck 45. Neck 45 is shaped such that recesses 47 and 48 are created where the arm assembly 33 and body 10 are connected.

Recesses 47 and 48 are shaped to receive a range of pins or wires that may be utilized during surgery. Recesses 47 and 48 may be the same or different shape depending on the arm and body design used, but in preferred embodiments may take a V-shape, U-shape or expanded U-shape.

In alternative embodiments, one or more arms 30 may be directly and independently connected to body 10 (not shown) at one end of the elongate arm and may be spaced apart or close together. Arms may be parallel, or may be angled from each other on the elongate axis of the arm 30. Arms preferably extend only from the convex face of an arcuate body, or one side only of a body 10. The optional one or more arms 30 may include one or more apertures 50 extending through the arm from the first arm face through to the second opposing arm face, such that a wire, rod or fixation device may be inserted into the aperture. The apertures are preferably cylindrical and may be perpendicular to the first and second arm faces, or may be angled.

Arms 30 may include any number of apertures, however 5-20 apertures on each arm are preferable, providing a range of options for insertion of a wire or rod. To ensure safety of the bone and prevent splitting or cracking, any aperture in the arm 30 at or near cutting channel 14 should be placed enough of a distance from cutting channel 14 to ensure adequate bone strength following the osteotomy. This may vary depending on the size of the guide and patient requirements, but for example in at TPLO procedure, this may be at least 5 mm for smaller animals, or 10 mm for larger dogs. Apertures may be 0.8 mm-6 mm in diameter, to suit a range of surgical pins or wires.

As seen in FIG. 8, measurement markings 52 may be marked on the faces or side walls of arms 30 to correspond to apertures 50. These allow the user to determine the correct placement of a fixation device for a particular surgical case, as will be discussed in further detail below.

Figure 9:
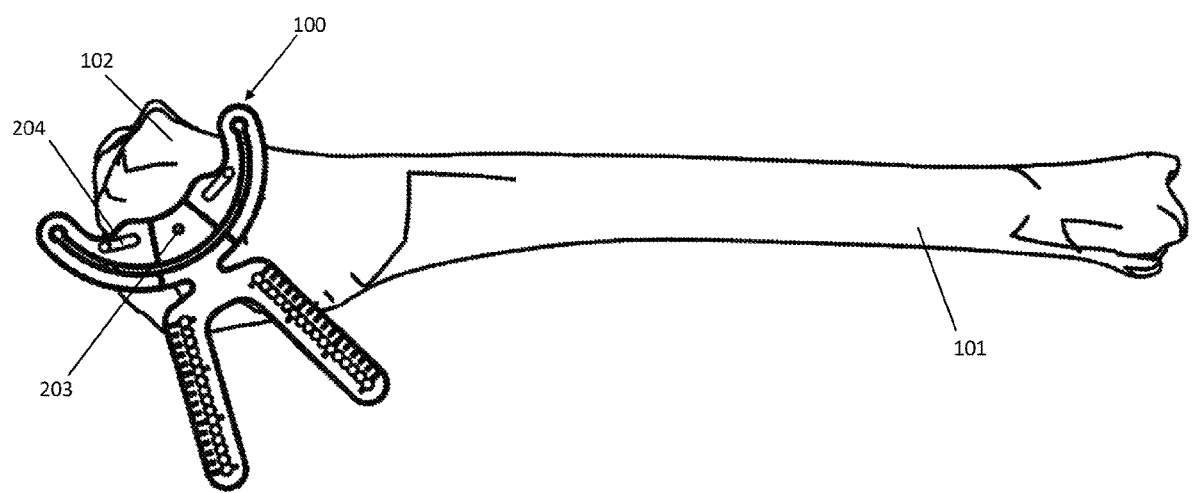
FIG. 9 shows the surgical guide of FIGS. 2, 3 and 5-8 positioned for use on a tibia.

The TPLO procedure when performed on a canine will now be described with reference to FIGS. 9 and 10. When guide 100 is used in a TPLO procedure, an initial surgical plan is decided for a specific patient, including the required location of the osteotomy for removing the proximal end 102 of the tibia 101. Once a plan has been developed, surgical pins 201, 202 are inserted into specific apertures in arm assembly 33, in line with predetermined anatomical landmarks. For a typical TPLO procedure, pins 201 and 202 will be offset relative to each other, with pin 201 inserted through an aperture in arm 31 near bridge portion 46, and pin 202 inserted into an aperture in arm 32 approximately halfway along the length on arm 32. This may change depending on the required osteotomy location.

Figure 10:
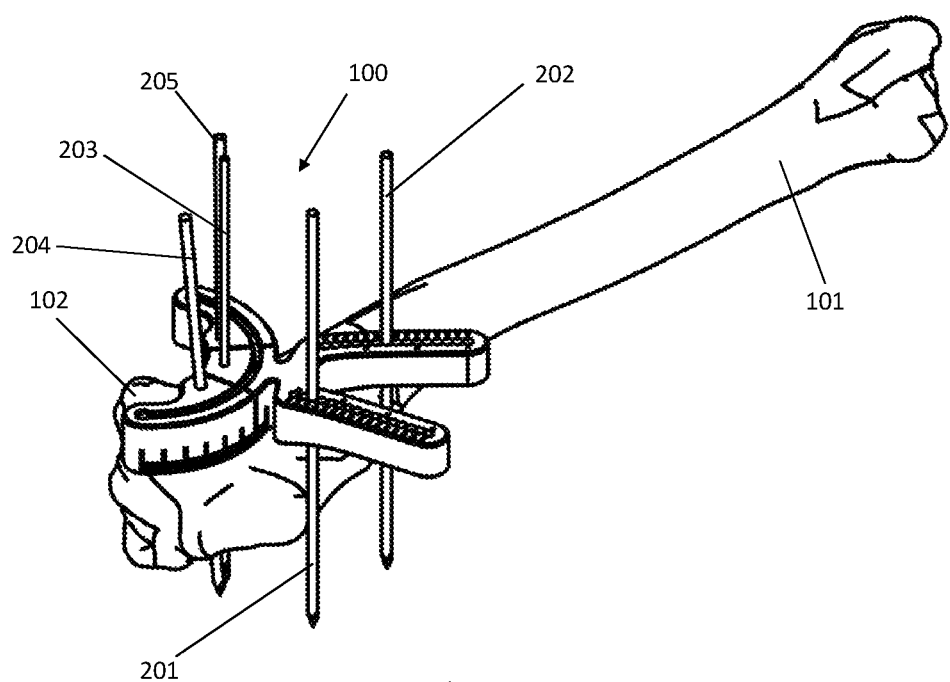
FIG. 10 shows a perspective view of the guide of FIG. 9 with fixation pins in position, securing the guide to the tibia.

Guide 100 is then placed over the proximal tibia with the second body face 12 abutting the patient bone and positioned such that pins 201 and 202 abut the edge of the tibia as seen in FIG. 10. Both pins 201 and 202 are positioned in apertures of arms 31 and 32 such that when the pins are aligned with predetermined anatomical locations, cutting channel 14 is in the required location for the osteotomy.

Following initial guide placement using pins 201 and 202, central locking pin 203 is inserted into the proximal tibia through aperture 17A in body 10 of the guide. This central locking pin fixes the guide in the correct position for the osteotomy. One or more oblique pins 203 and 204 can then be inserted to prevent further movement of the guide. Arm pins 201/202 may be removed at this point and reused as oblique pins 203/204 if required.

Once all the pins are in position and the guide is fixed, the pins may be trimmed to enable easier access to the guide to conduct the osteotomy.

A rotation mark is then made on the patient to indicate the degree of rotation required following the osteotomy. The rotation position may be marked using a pin or wire inserted to the end of the desired rotation point, or a tissue marker or osteotome may be used.

The osteotomy is then made by inserting a surgical blade through cutting channel 14 and removing the entire proximal tibia 102. Once the cut has been made, guide 100, which is secured to the proximal tibia 102 can be rotated, moving proximal tibia 102 to the new position. The degree of rotation required may be measured using the measurement guide 60 on body 10. As shown in an example in FIG. 10, point A on the measurement guide represents and is marked as a starting position, then guide 100 is rotated until point B on the measurement guide reaches the original marked starting position.

In other examples of guided rotation, a marker pin may be inserted as a starting point, then guide 100 and proximal tibia 102 rotated until the marker pin is received within recess 47 or 48 of the guide, preventing further rotation. In this example, the marker pin may be offset from the guide body, such that when the guide is rotated to contact the pin, the osteotomy is compressed due to the recess 47 or 48 in the guide aligning with the pin.

Once guide 100 is in the desired rotated position, an additional pin may be placed in the arm assembly 33 to hold the new position. A holding pin (not shown) may then be inserted through both the proximal tibia 102 and tibia 101 to retain the proximal tibia in the new position.

The newly positioned proximal tibia is then held in place using a TPLO plate (shown in FIG. 1). There are a variety of TPLO plates available for purchase such as those produced by De Puy Synthes, any of which would be suitable. Such a plate spans tibia sections 101 and 102 and holds them in position using locking and/or compression screws in known fashion.

The surgical guide of the present invention may be manufactured as a single use tool, from plastic (e.g. nylon) or other lightweight, durable material, or for multiple use from material such as stainless steel or other metal or plastic. Techniques such as machining or injection moulding may be used, as well as additive manufacturing. For patient specific guides having special anatomical features or contours built in, additive manufacturing is a preferable manufacturing method.

The guide has a number of advantages of known surgical guides, particularly for the TPLO procedure. The guide can be easily fixed in a wide range of different positions and angles by altering placement of pins on the arm assembly, making it suitable for a large cross section of animal species and sizes.

The arcuate body shape with contoured side walls provides the guide with a snug fit against the tibial medial condyle, and the apertures above the cutting line allow the resected tibial plateau to remain stable through rotation until fixed in the new position. The inclusion of rotation markers and the ability to manipulate the proximal segment via movement of the guide to aid in rotation all improve the accuracy and precision of the TPLO procedure.

The entire disclosures of all applications, patents and publications cited above and below, if any, are herein incorporated by reference.

Reference to any prior art in this specification is not, and should not be taken as, an acknowledgement or any form of suggestion that that prior art forms part of the common general knowledge in the field of endeavour in any country in the world.

Where in the foregoing description reference has been made to integers or components having known equivalents thereof, those integers are herein incorporated as if individually set forth.

It should be noted that various changes and modifications to the presently preferred embodiments described herein will be apparent to those skilled in the art. Such changes and modifications may be made without departing from the spirit and scope of the invention and without diminishing its attendant advantages. It is therefore intended that such changes and modifications be included within the present invention.

The invention claimed is:

1. A surgical guide for receiving and guiding a surgical instrument performing a bone osteotomy, the surgical guide including;
    a body, the body including a first body face and an opposing second body face adapted to abut the patient bone when in use, the first and second body faces separated by one or more side walls;
    at least one arcuate cutting channel curved around an axis substantially parallel to a vertical axis between the first and second body faces to guide the formation of an arcuate osteotomy in the bone from the first body face to the second body face, the arcuate cutting channel having a discrete length such that the arcuate cutting channel is bounded by the first and second body faces through which it extends;
    two or more apertures extending from the first body face through the body to the second body face, the apertures adapted to receive a fixation device;
    wherein the surgical guide includes one or more elongate arms or arm assemblies directly or indirectly connected to and extending from one side wall of the body;
    wherein the one or more elongate arms of the surgical guide consists of two elongate arms connected at a first end via a bridge portion to form a V or U-shaped arm assembly, the V or U-shaped arm assembly connected to the side wall of the body at or near the bridge portion of the V or U-shaped arm assembly; and
    wherein the body is arcuate in shape having a convex side wall and an opposing concave side wall, the V or U-shape arm assembly is centrally connected to the convex side wall.

2. The surgical guide of claim 1, wherein the opposing concave side wall is at least partially contoured.

3. The surgical guide of claim 1, wherein the surgical guide includes a second cutting channel extending through the body from the first body face to the second body face.

4. The surgical guide of claim 3, wherein the surgical guide includes one or more straight cutting channels and one or more arcuate cutting channels.

5. The surgical guide of claim 1, wherein the one or more elongate arms are integrally formed or removably connected with the body.

6. The surgical guide of claim 5, wherein the one or more elongate arms includes a first arm face and an opposing second arm face adapted to abut patient bone when in use, the first and second arm faces separated by one or more side walls; and one or more apertures extending from the first arm face through the one or more elongated arms to the second arm face, the apertures adapted to receive a fixation device.

7. The surgical guide of claim 6, wherein the one or more elongate arms are directly or indirectly connected to the body such that the first body face and the first arm face are substantially parallel with each other.

8. The surgical guide of claim 5, wherein each arm including between 1-20 cylindrical apertures spaced along the length of each arm.

9. The surgical guide of claim 1, wherein the U or V-shaped arm assembly is connected to the convex side wall at the bridge portion of the V or U-shape body via a neck.

10. The surgical guide of claim 9, wherein the neck is shaped to create one or more recesses between the arm assembly and the body of the guide.

11. The surgical guide of claim 1, wherein the two or more apertures comprises three cylindrical apertures, the three cylindrical apertures positioned on a same side of the arcuate cutting channel.

12. The surgical guide of claim 11, wherein the body includes two angled cylindrical apertures converging towards a central cylindrical aperture located between the two angled cylindrical apertures.

13. The surgical guide of claim 1, wherein the body includes at least one side wall including contours in the wall.

14. The surgical guide of claim 1, wherein the body includes rotational measurement markings on one or more side walls.

15. A method for guiding an osteotomy tool using the surgical guide of claim 1, the method including the steps of;
 a) determining one or more preferred osteotomy positions on a patient body;
 b) aligning the surgical guide with an anatomical location on a patient;
 c) fixing the surgical guide in position on the patient using one or more apertures on the surgical guide;
 d) guiding the osteotomy tool through or partially through the the at least one arcuate cutting channel in the surgical guide.

16. A method for making an osteotomy during a canine tibial plateau levelling osteotomy procedure using the surgical guide of claim 1, the method including;
 a) determining one or more preferred osteotomy positions on a canine tibia;
 b) aligning the surgical guide with an anatomical location on the canine;
 c) fixing the surgical guide in position on a tibial plateau of the canine using one or more apertures on the surgical guide;
 d) guiding an osteotomy tool through or partially through the at least one arcuate cutting channel in the surgical guide to fully remove the tibial plateau;
 e) rotating the tibial plateau and the surgical guide based on a predetermined mark on the surgical guide;
 f) securing the tibial plateau in a new location using a fixation tool; and
 g) removing the surgical guide.

* * * * *